(12) United States Patent
Imam et al.

(10) Patent No.: US 8,865,214 B1
(45) Date of Patent: Oct. 21, 2014

(54) BIOACTIVE GYPSUM STARCH COMPOSITION

(75) Inventors: Syed H. Imam, Walnut Creek, CA (US); Gregory M. Glenn, American Canyon, CA (US); Farooqe Azam, Peshawar (PK)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/485,877

(22) Filed: May 31, 2012

Related U.S. Application Data

(60) Provisional application No. 61/491,888, filed on May 31, 2011.

(51) Int. Cl.
*A61K 9/26* (2006.01)
*A61K 9/14* (2006.01)
*A01N 63/00* (2006.01)
*A01N 63/04* (2006.01)
*C05D 3/00* (2006.01)

(52) U.S. Cl.
CPC ............. *A01N 63/04* (2013.01); *A01N 63/00* (2013.01); *C05D 3/00* (2013.01)
USPC ............ 424/469; 424/485; 424/486; 504/117

(58) Field of Classification Search
None
See application file for complete search history.

(56) References Cited

U.S. PATENT DOCUMENTS

| | | | |
|---|---|---|---|
| 2008/0107689 A1* | 5/2008 | Seiskari | 424/234.1 |
| 2012/0015805 A1* | 1/2012 | Goodwin | 504/100 |

* cited by examiner

*Primary Examiner* — Alton Pryor
(74) *Attorney, Agent, or Firm* — John D. Fado; Howard V. Owens, Jr.

(57) ABSTRACT

Bioactive formulations and methods of use comprising a gypsum biopolymer matrix and soil beneficial microorganisms are described herein.

6 Claims, 11 Drawing Sheets

BIOACTIVE GYPSUM STARCH COMPOSITION

FIELD OF THE INVENTION

The present invention relates to bioactive compositions composed of a porous matrix of gypsum, starch and microorganisms.

SUMMARY OF THE INVENTION

Herein is described matrix polymer compositions comprising a biopolymer and gympsum as a porous matrix for the containment of soil beneficial microorganisms.

A further embodiment is a method for increasing plant biomass of an agricultural crop by application to the soil of the plant a matrix polymer composition comprising a porous biopolymer-gypsum matrix containing soil beneficial microorganisms.

BACKGROUND OF THE INVENTION

Multiple applications of synthetic chemicals including fertilizers and fungicides are typically used to obtain high crop yields. However, low cost, natural methods of providing soil nutrition and resistance to plant diseases could be developed. Various soil microbes have been shown to help plants fix nitrogen, solubilize soil phosphate, improve nutrient availability, resist diseases (biocontrol agents) and adapt to environmental stresses. Provision of a low cost environmentally compatible alternative to synthetic fertilizer is therefore desired utilizing positive soil microorganisms is therefore desired.

DETAILED DESCRIPTION OF THE INVENTION

Figure 1:
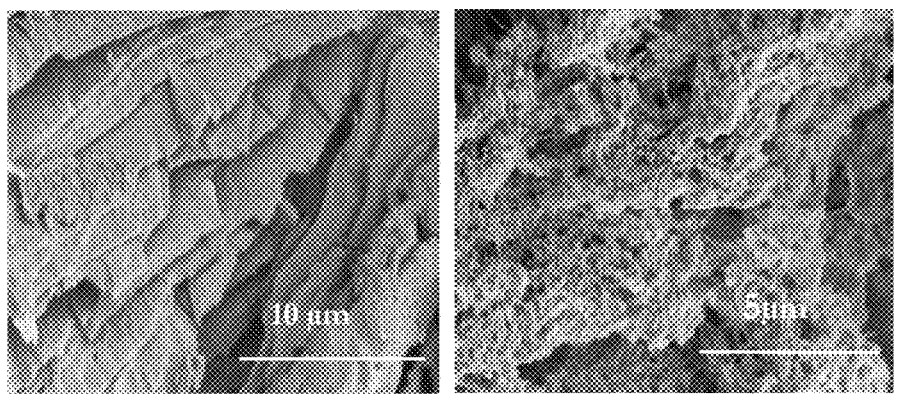
FIG. 1 is a photo of gypsum starch matrix architecture as viewed under a scanning electron microscope (SEM).

The present invention will now be described by reference to more detailed embodiments, with occasional reference to the accompanying tables. This invention may, however, be embodied in different forms and should not be construed as limited to the embodiments set forth herein Unless otherwise indicated, all numbers expressing quantities, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement.

An embodiment of the invention describes a porous matrix produced by compounding or mixing $CaSO_4.H_2O$ (gypsum), and starch. A preferred embodiment is the gypsum starch matrix in combination with microorganisms wherein the matrix serves as a scaffold for the growth and distribution of microorganisms that aide in the growth and development of plants and/or protect plants from diseases. Five classes of microbes are expected to be the part of the final formulation, e.g., (1) the microbes that can fix nitrogen, (2) solubilize soil phosphate, (3) produce growth promoting substances, (4) make essential minerals and vitamins available to the germinating plant, and finally, (5) microbes that serve as biocontrol agents to prevent diseases and infections. Positive microorganisms which may be utilized include but are not limited to *Pseudomonas putida, Rhizobium meliloti, Azospirillum* sp, *Epicoccum nigrum, Stachybotrys atra, Trichoderma hamatum, Bacillus subtilis, Gliocladium virens* and *Talaromyces flavu*, see tables 1 and 2.

TABLE 1

PG (Growth Promoting) Granules

| Microbe | Functionality |
| --- | --- |
| *Pseudomonas putida* | Produce growth hormone and solubilize P |
| *Rhizobium meliloti* | Fix N2 |
| *Azospirillum* sp | Fix N2 |
| *Epicoccum nigrum* | Synthesize humic compounds, which chelate multivalent cations such as Mg 2+, Ca 2+, and Fe 2+ |
| *Stachybotrys atra* | Synthesize humic compounds |
| *Trichoderma hamatum* | Produce compounds having biocontrol activity against soil borne fungal pathogens, especially, for controlling the *Fusarium* wilt diseases. |

TABLE 2

DP (Disease Protection) Granules

| Microbe | Functionality |
| --- | --- |
| *Pseudomonas putida* | Produce growth hormone and solubilize P |
| *Azospirillum* sp | Fix N2 |
| *Aspergillus terreus* | Synthesize humic compounds |
| *Trichoderma hamatum, Gliocladium virens*, and *Talaromyces flavu* | Produce compounds having biocontrol activity against soil borne fungal pathogens, especially, for controlling the *Fusarium* wilt diseases. |
| *Bacillus subtilis* | Produce compounds to suppress seedling diseases and long-term chronic diseases of rhizosphere in crops. |

Gypsum is an inexpensive compound used mostly in building materials as well as a soil additive in agriculture and horticulture as a source of calcium and sulphur fertilizer and to improve the soil structure for better drainage and plant growth. The starch used may be in a gelatinized or un-gelatinized form derived from variable botanical sources. In addition to starch, other polysaccharides, polypeptides, fatty acids and biological macromolecules could also be used in combination with gypsum to produce such matrices. Additional polymers which may be used are cornstarch, pregelatinized wheat starch, derivatized starch, cellulosics, polylactic acid (PLA), poly-hydroxybutyrate/velerate (PHBV), polyvinyl alcohol (PVA). In one case, starch and PVA were crosslinked using hexamethoxymethylmalamine (HMMM) as a cross-linker. Additives which may be used are nano-clays (such as closites and bentonite) and perlite, a naturally occurring siliceous rock (volcanic glass) containing about 75-80% silicon dioxide—$SiO_2$ and 10-15% aluminum dioxide—$Al_2O_3$).

The composition of gypsum and starch forms a three dimensional matrix containing pores and tunnels of macro, micro and nano size. The composition may be in a variety of shapes and forms including granules, pellets and strands. The matrix can be achieved via extrusion using either single-screw or twin-screw extruders as well as pasta making machineries with or without any shear force. Sprayable formulations and thin films, either extruded, or pressed or compressed are also achievable. Such matrices are ideal for encapsulation of chemicals, biological agents, enzymes, active microbes, and could serve as filtration aid for liquids and organic solvents. Gypsum is currently used in construction/building materials such as dry-walls and sheet rocks, etc. In the presence of starch, pores and tunnels in the gypsum decrease the overall density of the matrix.

A proposed structure for the product reaction is shown below. Under the reaction conditions, the hydroxyl oxygens of the gelatinized starch were behaving as base moieties providing coordination sites for the $Ca^{2+}SO_4^{2-}$. Thus depending on the availability of cationic species, bridging and cross linking of starch chains result through the $Ca^{2+}$ ions. This should generate three dimensional vacuoles or tunnels that can entrap or filter smaller molecules and microbes. The stoichiometry of the reagents used, the degree of mixing and the temperature of the process would determine the uniformity of the produced pores/tunnels in the gypsum-starch product.

The matrix is extremely resilient to a variety of extreme conditions such as heat, UV, salt concentration, and is functional under wide range pf pHs. The matrix is also physically strong; it swells and expands in water, but resists disintegration. Even after submersion in water for over 72 h, compressive strength tests showed that 35 kg of weight was required to achieve 50% compression. Given these physical properties, an additional embodiment of the invention is the use of the gypsum-starch matrix in building materials and as a filtration aid, particularly, for removing water and other undesirable byproducts from biofuels.

Matrix Development

Two types of polymeric matrices are described herein. A first matrix (Matrix-I) was based on Perlite particles that were infused with pregelatinized wheat starch containing selected microbes along with the carbon source (glucose and/or enriched media) to support initial microbial growth. Slow starch degradation over an extended period of time would ensure a steady and sustained supply of nutrient source for the later growth. These particles were further coated in a granulator with either gypsum or bentonite nano-clays (FIG. 1A). A SEM of a cross-section showed great capacity of Perlite to allow the infusion of starch particles into its micro-cavities without (FIG. 1B) and with encapsulated starch (FIG. 1C).

A Second matrix (Matrix-II) involved blending of starch with natural mineral, gypsum (calcium sulphate di-hydrate—$CaSO_4.2H_2O$). Gypsum (also known as "plaster of Paris") is extensively used in agriculture and horticulture as a source of calcium and sulphur fertilizer. As an added advantage, it also improves soil structure for better drainage and plant growth. About 5-10% pre-gelatinized starch powder (dry-weight basis) is mixed with natural mineral gypsum (calcium sulphate di-hydrate—$CaSO4.2H2O$). Freeze-dried powder containing microbial cells was added to the starch-gypsum mix (final cell-density was approximately 1×104 cells/gram of mix). Ingredients were mixed for about 5 minutes in a mechanical mixer under the herein described torque conditions and the final moisture content was brought to between 7-10%. The Mixture was extruded in the form of noodles at room temperature (23° C.). Noodles were dried for 15-30 minutes at room temperature and pelletized to an appropriate diameter using a commercial plastic-pelletizer. Pellets were placed in plastic bags and stored for subsequent use.

Before adding gypsum in above formulation, it is preheated to about 160° C., which drives off some water from gypsum changing calcium sulphate di-hydrate (di means two) to calcium hemi-hydrate (hemi means half) as described here:

CaSO4.2H2O→CaSO4.½H2O+1½H2O

Figure 2:
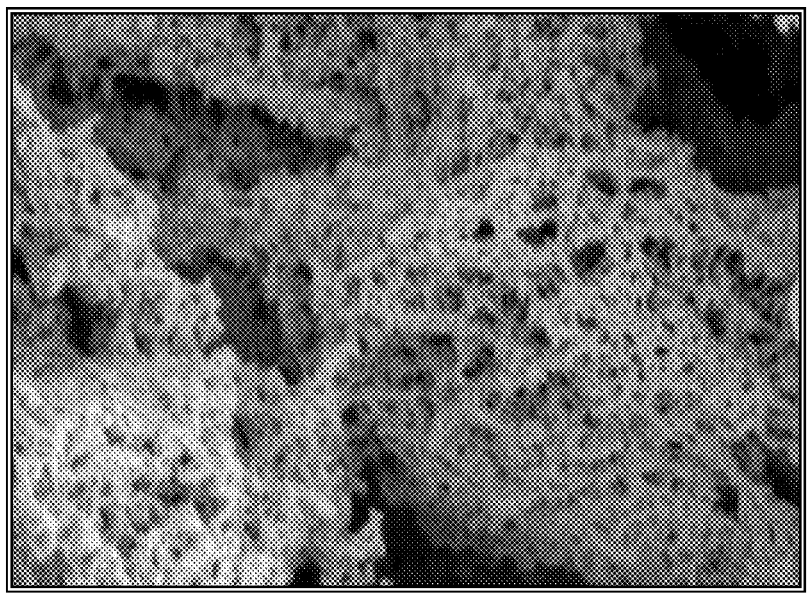
FIG. 2 is a SEM view of the matrix at a higher magnification.

When water is added back, hemi-hydrated form turns back to gypsum and sets hard within 20-30 minutes yielding a highly porous but hardened matrix containing nanopores and channels (see SEM of FIG. 2A). Gypsum (also known as "plaster of Paris") is extensively used in agriculture and horticulture as a source of calcium and sulphur fertilizer. As an added advantage, it also improves soil structure for better drainage and plant growth. When heated to about 160° C., heat drives off some water from gypsum changing calcium sulphate di-hydrate (di means two) to calcium hemi-hydrate (hemi means half) as described here: $CaSO_4.2H_2O \rightarrow CaSO_4.½H_2O+1½H_2O$. However, if starch, nutrients, microbes and other additives are added along with water, gypsum yields a highly porous but hardened matrix containing nanopores (FIG. 2B). The size of the pores in the starch-gypsum matrix ranged between 10-250 nm.

Pores in the matrix are controlled by exerting a moderate amount of torque during the processing of the material in the extruder. Torque is the amount of force required to rotate the starch-gypsum type of material in the screw of the barrel. Length of the screw in the extruder is directly proportional to the amount of torque required to rotate the material. Therefore, the exertion of torque (directly or proportionally) from 1 to 3 Nm (Newton meters), preferably 1.5-2.0 Nm (Newton meters) provide a shorter residence time for material processing and confer the aforementioned porosity. Thus, smaller torque in conjunction with shorter residence time results in a moderately densified matrix material and allows the development of network of pores and channels. Higher torque, greater than 3-4 Nms tends to yield densified materials with little or no pores.

In view of its architecture, the matrix is ideal for the entrapment of microbes, allowing their growth and metabolic activities to continue unhindered (FIG. 2C). Additionally, pores are numerous and large enough to permit water diffusion as well as unrestricted flow of active compounds produced by the entrapped microbes. Such internal structure will also entrap some bacteria physically within the matrix for a very long time.

Apart from physical and functional attributes, starch-gypsum based matrix can be produced in large quantities utilizing kitchen aid Hobart® mixer equipped with simple pasta-making attachments. Noodles were collected and dried for 25 minutes (semi-hardened) at room temperature (24° C.) and palletized. Pellets were further dried overnight at 40° C. and stored in a closed container for future use. Procedure is described in a sequence of photographs presented in FIG. 3. It is important to note that gypsum is a very inexpensive fertilizer mineral available world-wide.

Matrix Selection, Characterization and Optimization

The matrices of the invention conform to the ideal fertilizer by obeying the characteristics of (a) stimulate nutrient uptake in plant (b) support plant growth (c) improve soil structure (d) promote decomposition of other organic wastes/residues in soil and (e) provide biological control of soil-borne diseases. Particularly, in microbes-based fertilizer, the matrix allows the biosynthesis of physiologically active substances by microbes and their diffusion in the vicinity of rhizosphere or in soil.

Immobilizing of soil beneficial microbes and isolation from native competing microbes, promoting their subsequent growth; retention of shape and integrity under irrigation conditions for 2-3 days; and exit of water as well as bioactive substances produced by microbes inside the matrix while retaining most of the microbes still encapsulated is achieved by use of the herein described matrix polymer. The matrix may achieve (a) the physical shape and form quite similar to the existing commercial granular formulations, (b) exhibit functionality that is long-lasting and (c) is viable for several successive crops (about 2-3 years). Table I outlines the behavior of individual constituents alone and in combination with other polymers with respect to their processing conditions, swelling, submergence, physical integrity (shape-retention) and weight increase upon exposure to water for extended period of time (>72 hours). Initial screening successfully identified those formulations that disintegrated due to the lack of cohesiveness or binding between the materials and/or floated upon exposure to water.

Figure 4:
FIG. 4 is a SEM cross section showing encapsulated microbes growing inside the matrix upon activation in water.

A further embodiment of the invention is the use of various combinations of starch, gypsum, bentonite and PVA (Table I, bottom three). Among these, starch in combination with gypsum appears to be the most economical and simply processed formulation, which also met all of the conditions that were set forward for an efficient matrix and deemed critical for high performance (Table I, highlighted formulation). This particular formulation swelled in water and gained roughly 72% in weight, which is advantageous as this will allow more space for microbes to grow as well as exchange of fluids and materials in and out of the matrix. The degree of swelling and disintegration observed upon exposure of matrix in water was quite variable depending on the individual component and their polymeric blends (FIG. 4).

Figure 5:
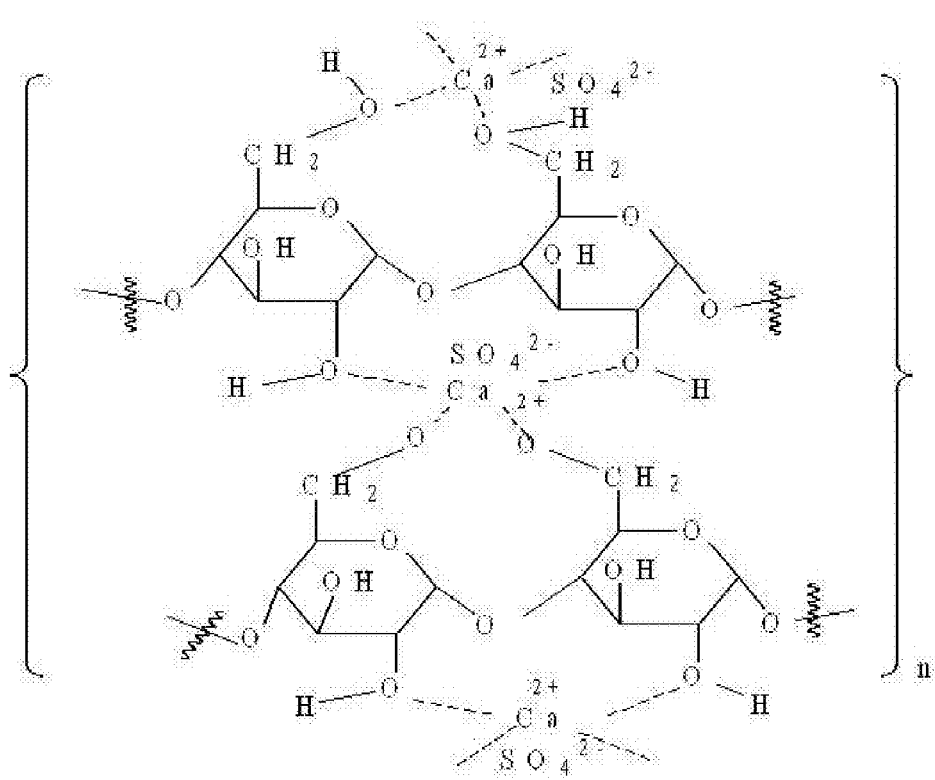
FIG. 5 is a drawing of the proposed mechanism of gypsum starch interaction and the resulting matrix formation.

Starch is present in the gypsum/starch based formulation at a concentration of 6-10% (w/w), with gypsum at 50-90% (w/w). Various gypsum/starch based formulations swelled in water when exposed for 72 h at 23° C. Water absorption ranged between 50-90% of its total mass (FIG. 5A). Upon drying, pellets reflected a loss of mass between 10-14% of the total initial mass (FIG. 5B). The compressive strengths of the unexposed pellets were measured by Texture Analyser (TAXT-2, Texture Technologies Corp., Scarsdale, N.Y.) and compared with the pellets that have been exposed to water for 72 h and dried subsequently at 23° C. Bonding between starch-gypsum were so efficient that it required 12 kg of weight to crush the unexposed pellets. After 72 hours of immersion in water, pellets remain intact and strongly bonded, retaining almost half of the original bonding strength (FIG. 5C). Interestingly, size of the pellets exposed in water and dried at 23° C., did not change very much (FIG. 5D). Additionally, the pH of the water in which pellets were immersed for 72 hours fluctuated between pH 7.0-pH 8.0 (FIG. 5E).

Figure 3:
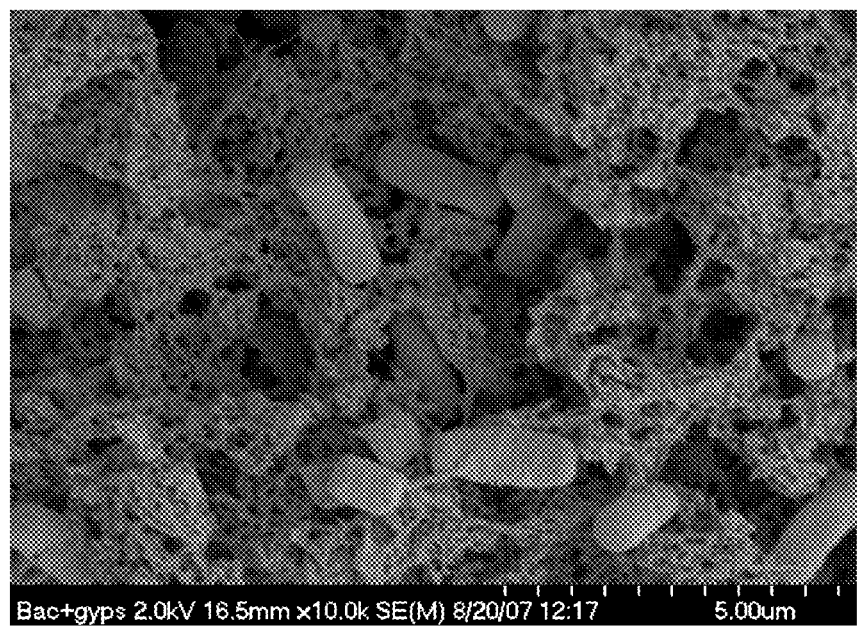
FIG. 3 is a SEM cross section showing encapsulation or entrapment of biologically active microbes in the matrix.
Figure 6A:
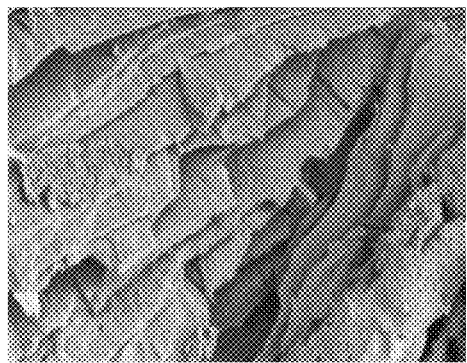
FIG. 6A-C are photos of gypsum starch matrix architecture as viewed under a scanning electron microscope (SEM) at different magnifications.
Figure 6B:
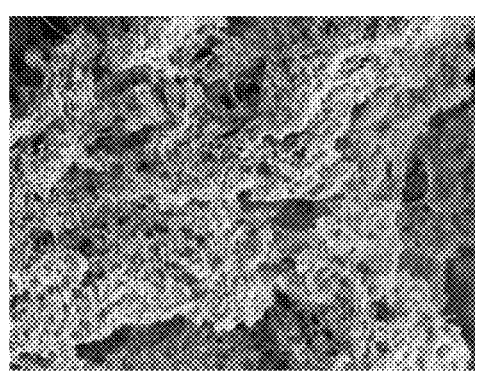
Figure 6C:
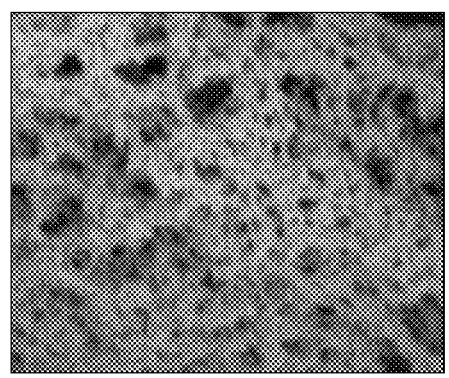

Molds or extrusion equipment available to one of skill in the art may be utilized for formation of the matrix; however, extrusion is preferred. When similar formulations were compounded and extruded (through pasta machine; see FIG. 3), the pellets had properties quite similar to non-extruded samples, but with much superior compressive strength and water resistance. Both of these are highly desirable properties. Extruded pellets are shown in FIG. 3 (gypsum/starch, 2:1 ratio). The data on the mass increase due to water absorption, loss of mass, pH effect on the medium and compressive strengths before and after prolonged submergence of up to 120 hours are provided in FIG. 6. Such formulations exhibited a significantly elevated compressive strength both before and after submergence (33 kg and 23 kg, respectively). Also, Pellets seem more stable with respect to any loss of mass due to extended submergence in water. Compressive strength is a good indicator of cohesiveness or integrity of these delivery systems and their long-term persistence in the field under water and upon drying. Also shown in these figures are the data where pellets were either cryo-ground into smaller granular form or pellets where gypsum was extruded along with additives equilibrated Perlite.

TABLE 3

Characteristics of various components alone or in combination used for developing a fertilizer matrix.†

| Component(s) | Processing Conditions | Water-Absorption/Swelling | Submerged/Floated in Water | Shape Retention upon Extended Exposure in Water | % Weight Increase in Submerged Water |
|---|---|---|---|---|---|
| Starch* | cold | yes | floated | no | |
| PVOH | hot | no | submerged | yes | |
| Perlite | cold | no | floated | yes | |
| Bentonite | cold | no | floated | no | |
| Gypsum | cold | no | submerged | no | |
| Gypsum + PVOH | cold | no | submerged | yes | 14 |
| Gypsum + Starch | cold | yes | submerged | yes | 72 |
| Gypsum + Starch/Benton. | cold | yes | submerged | yes | 70 |
| Bentonite + Starch/PVOH | hot | yes | submerged | yes | ND |

*Pre-gelatinized wheat starch, ND = not determined
†Exact compositions of formulations are not provided due to the IP considerations.

Encapsulation Matrix for Microbial Growth and Proliferation

Figure 7:
FIG. 7 is a photo of the impact of microbial based starch encapsulated fertilizers on plant growth in a green-house.
Figure 8:
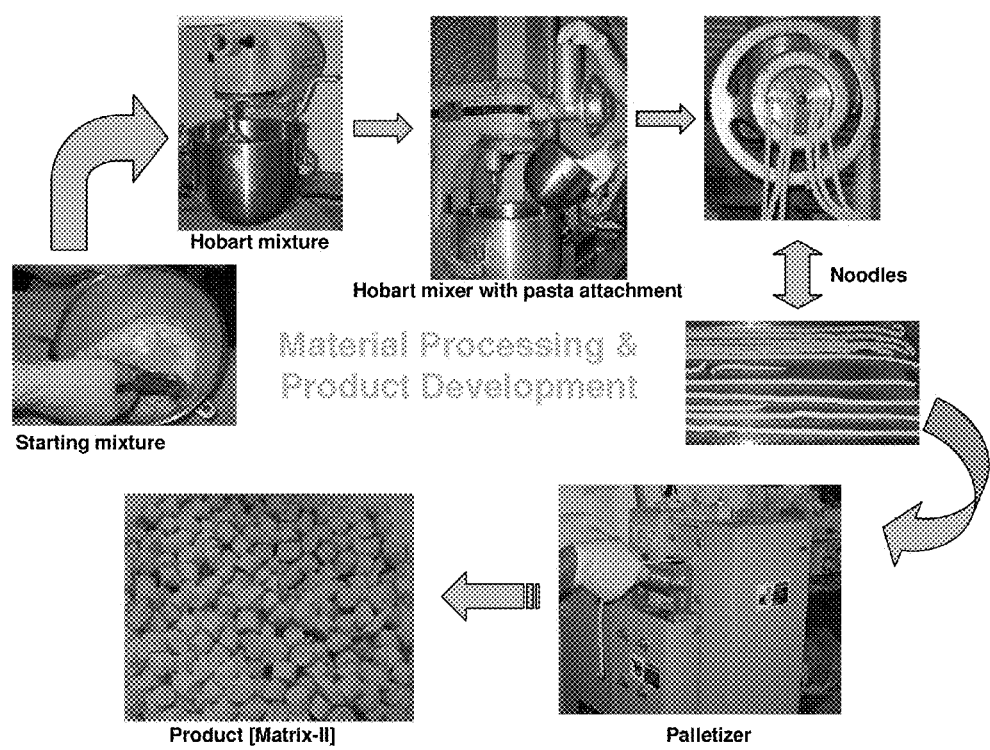
FIG. 8 is a photo diagram of the processing method.
Figure 9A:
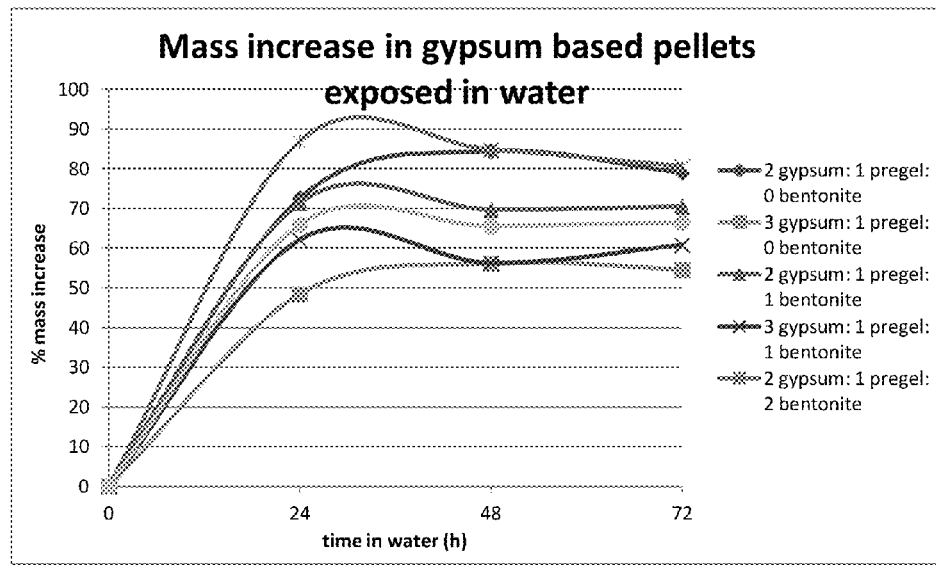
FIG. 9A-E are charts of mass and pH changes of various gypsum formulations.
Figure 9B:
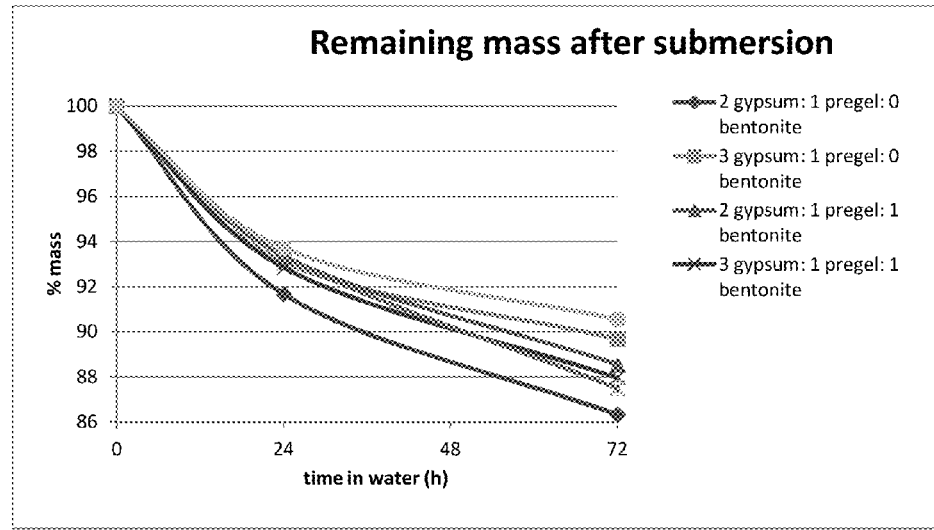
Figure 9C:
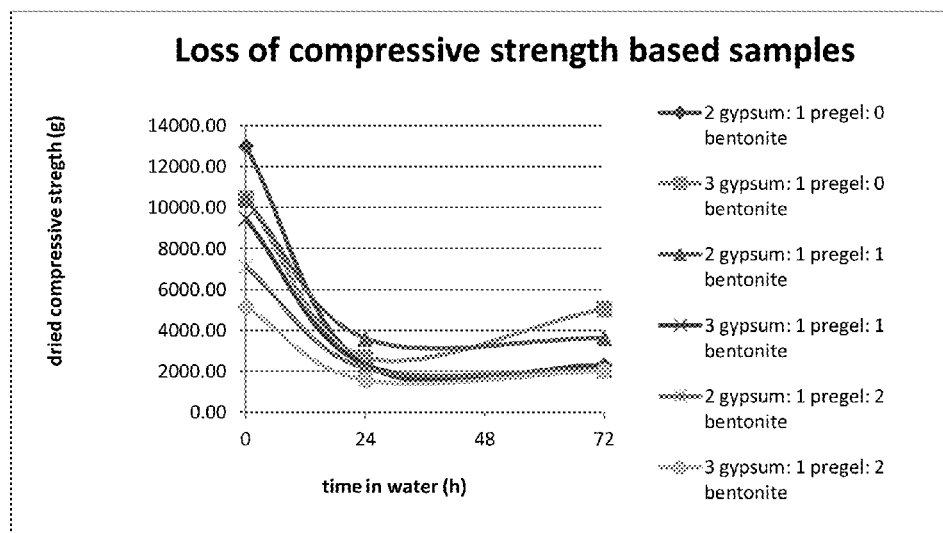
Figure 9D:
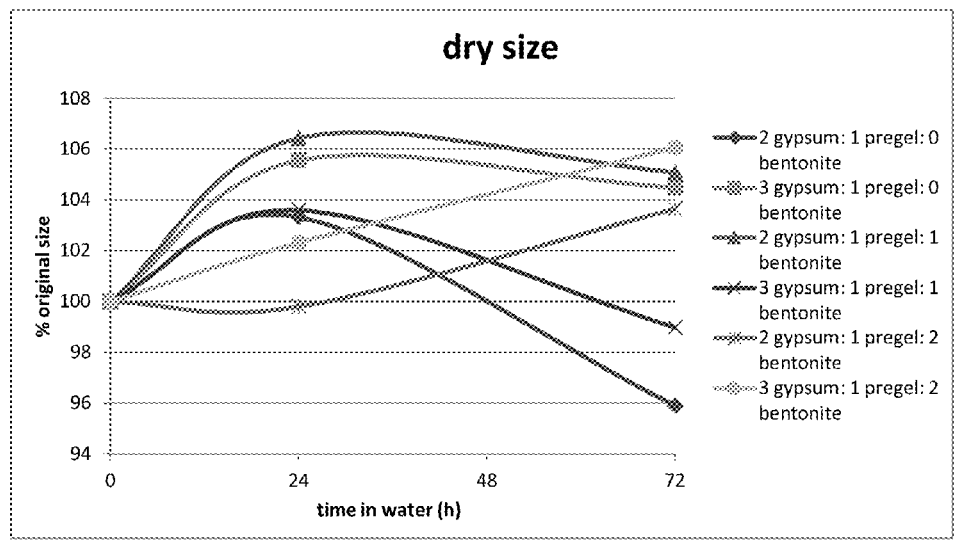
Figure 9E:
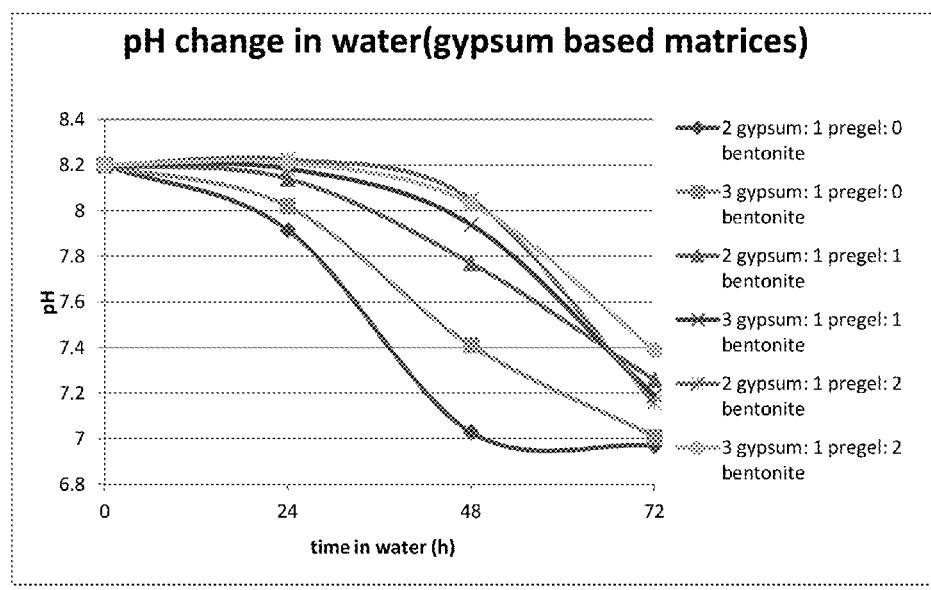

Selected gypsum-starch encapsulation matrix (extruded) was evaluated to confirm their functionality with respect to growth and proliferation of encapsulated microbes. All of the 5 beneficial microbial strains that will be part of the final formulations are being produced by Dr. Farooq Azam in Pakistan and Dr. Mark Jackson at NCAUR-USDA, Peoria, Ill. The use of these microbes in the ultimate formulation is planed for late next year. However, as a proof of concept, cultures of a common spore-forming soil bacterium, *Bacillus* RSM2 were grown in an enriched medium overnight and added to the formulation ($1 \times 10^4$ cells/gram of solids). These microbes are shown (SEM) embedded within the gypsum-starch matrix in a cross section of a pellet. This microbe is small and rod-shaped, but under stress may form spores and become rounded (FIG. 7). Pellets of formulation containing *Bacillus* RSM2 were submerged in the test tube containing tap water for 24 hours exhibited a substantial growth of microbes both inside (FIG. 7) and out side the matrix (FIG. 7). The water in the test tube became turbid, and microbial density in the water approached up to $1 \times 10^6$ cells/ml, whereas, control formulation (7-left) showed no growth at all. Standard microbiological methods were used through out. Cell density was determined using a combination of optical density as well as by pour plate methods. From the data, it was quite obvious that the selected gypsum-starch matrix not only allowed microbial growth and proliferation but also freely exchanged metabolites (yellowish-colored metabolites) from the encapsulation matrix in to the outer medium. Assessing from the physical and internal structure of the matrix and its behavior when exposed to water for an expanded period of time, it is expected that the selected consortia of planned microbes would also work in the similar fashion.

Starch-Gypsum matrices in the form of pellets retain 80-90% of the compressive strength conferring cohesive and protectant qualities under a variety of extreme environmental conditions. The impact of temperature (ranging from −80-60° C.), salt concentrations (0-0.5M), humidity (5%-100%) had little or no impact on microbial growth and proliferation. Under all conditions microbial cells remained viable and proliferated. Additionally, UV exposure (dose) that is typically fatal for *Bacillus* RSM2 not only protected the microbes within the matrix but showed enhanced microbial growth. Low or high pH values showed little growth inhibition. Thermal degradation of the matrix requires heating the matrix at 100° C. for 24 hours, which also counter productively inhibits microbial growth.

Green-House Studies on Microbes Based Fertilizer Matrix and its Impact on Plant Growth and Root Development Table 4 provides information on the some of the microbes that were utilized in the green-house studies.

TABLE 4

Bacterial and fungal strains identified for encapsulation

| Microorganism | Functionality |
|---|---|
| Bacteria | |
| *Pseudomonas fluorescence* | Growth hormone and *ACC deaminase producer |
| *Pseudomonas putida* | Growth hormone and ACC deaminase producer, P-solubilizing |
| *Serratia marsescence* | Growth promoting, Exopolysaccharide producing |
| *Rhizobium meliloti* | $N_2$-fixing |
| *Burkholdaria* sp | Growth promoting, Exopolysaccharide producing |
| *Azospirillum* sp | $N_2$ fixing |
| Fungi | |
| *Epicoccum nigrum* | Capable of synthesizing humic compounds |
| *Stachybotrys atra* | Capable of synthesizing humic compounds |
| *Aspergillus terreus* | Capable of synthesizing humic compounds |

Use of the starch gypsum matrix within a variety of agricultural crops is contemplated including food, feed, fiber and specialty crops. Green-house screenings were conducted with cereal and wheat plants. However, numerous other crops were also evaluated. Comparative biomass production in some of the crops evaluated under the green-house conditions is presented in FIG. 7. All factors and conditions being equal, in all cases, plants treated with microbial fertilizers had significantly higher biomass produced compared to control values. Furthermore, the NIAB laboratory has successfully shown in the green-house studies (data not shown) that the soil treated with microbial fertilizer can be reused for growing 2-3 successive crops without supplementing it with any additional fertilizer, demonstrating that encapsulated microbes in the matrix can survive and become active under conditions conducive for their growth.

What is claimed:

1. A matrix polymer composition consisting essentially of a porous starch-gypsum polymer matrix wherein the starch-gypsum matrix polymer has a compressive strength of about 33 kg to about 35 kg and soil beneficial microbes are held therein.

2. The composition of claim 1, where the microbes are selected from the group consisting of *Pseudomonas putida, Rhizobium meliloti, Azospirillum* sp, *Epicoccum nigrum, Stachybotrys atra, Trichoderma hamatum, Bacillus subtilis, Gliocladium virens* and *Talaromyces flavu*.

3. The composition of claim 1, wherein the pores of the polymer are 10-250 nm in diameter.

4. The composition of claim 1, wherein the starch is at a concentration of 6%-10% of the polymer composition.

5. A method for increasing plant biomass of an agricultural crop by application to the soil of the plant a matrix polymer composition consisting essentially of a starch-gypsum matrix polymer wherein the starch-gypsum matrix polymer has a compressive strength of about 33 kg to about 35 kg and wherein soil beneficial microbes are held therein.

6. The method of claim 5, wherein the soil beneficial microbes are selected from the group consisting of *Pseudomonas putida, Rhizobium meliloti, Azospirillum* sp, *Epicoccum nigrum, Stachybotrys atra, Trichoderma hamatum, Bacillus subtilis, Gliocladium virens* and *Talaromyces flavu*.

* * * * *